(12) United States Patent
Steinbach et al.

(10) Patent No.: US 8,034,030 B2
(45) Date of Patent: *Oct. 11, 2011

(54) MULTI-RESERVOIR IMPLANTABLE PUMP WITH VARIABLE FLOW RATE CAPABILITIES

(75) Inventors: Bernd Steinbach, Friedberg (DE); Klaus Lederer, Naples, FL (US)

(73) Assignee: Palyon Medical (BVI) Limited (VG)

( * ) Notice: Subject to any disclaimer, the term of this patent is extended or adjusted under 35 U.S.C. 154(b) by 1492 days.

This patent is subject to a terminal disclaimer.

(21) Appl. No.: 11/137,284

(22) Filed: May 25, 2005

(65) Prior Publication Data
US 2006/0271022 A1 Nov. 30, 2006

(51) Int. Cl.
*A61M 1/00* (2006.01)
*A61M 37/00* (2006.01)
(52) U.S. Cl. .................. 604/153; 604/133; 604/141
(58) Field of Classification Search ............ 604/69, 604/93.01, 145, 151, 153, 246, 288.01–288.04, 604/131–133, 140, 141, 249, 890.1–892.1
See application file for complete search history.

(56) References Cited

U.S. PATENT DOCUMENTS

| | | | |
|---|---|---|---|
| 2,245,350 A | 6/1941 | Marshall | |
| 3,951,147 A | 4/1976 | Tucker et al. | |
| 4,003,379 A | 1/1977 | Ellinwood, Jr. | |
| 4,193,397 A | 3/1980 | Tucker et al. | |
| 4,258,711 A | 3/1981 | Tucker et al. | |
| 4,544,371 A | 10/1985 | Dormandy, Jr. et al. | |
| 4,548,607 A | 10/1985 | Harris | |
| 4,588,394 A | 5/1986 | Schulte et al. | |
| 4,634,427 A | 1/1987 | Hannula et al. | |
| 4,668,231 A | 5/1987 | de Vries et al. | |
| 4,699,615 A | 10/1987 | Fischell et al. | |
| 4,714,462 A | 12/1987 | DiDomenico | |
| 4,747,832 A | 5/1988 | Buffet et al. | |
| 4,813,951 A | 3/1989 | Cannon | |
| 4,828,551 A | 5/1989 | Gertler et al. | |
| 4,838,887 A | 6/1989 | Idriss | |
| 4,898,584 A | 2/1990 | Borsanyi et al. | |
| 4,908,019 A | 3/1990 | Urquhart et al. | |

(Continued)

FOREIGN PATENT DOCUMENTS

DE 20311947 U1 11/2003
(Continued)

OTHER PUBLICATIONS

Udelsman et al., "Intraperitoneal delivery of insulin via mechanical pump:surgical implications", Mar. 3, 2000, Langenbeck's Arch Surg (2000) 385:367-372.

(Continued)

*Primary Examiner* — Nicholas D Lucchesi
*Assistant Examiner* — Nathan R Price
(74) *Attorney, Agent, or Firm* — Lerner, David, Littenberg, Krumholz & Mentlik, LLP

(57) ABSTRACT

A multiple reservoir or chambered implantable pumps is disclosed. The pump according to the present invention is particularly useful in allowing for multiple constant flow rates to be provided from an otherwise constant flow implantable pump. The pump is also useful in allowing for housing of multiple active substances. A multiple reservoir implantable pump is also disclosed, which has at least one chamber capable of providing a constant flow rate and at least one chamber capable of being utilized for patient controlled injections.

25 Claims, 7 Drawing Sheets

U.S. PATENT DOCUMENTS

| | | | |
|---|---|---|---|
| 4,969,873 | A | 11/1990 | Steinbach et al. |
| 5,011,477 | A | 4/1991 | Winchell et al. |
| 5,085,644 | A | 2/1992 | Watson et al. |
| 5,085,656 | A | 2/1992 | Polaschegg |
| 5,152,753 | A | 10/1992 | Laguette et al. |
| 5,167,633 | A | 12/1992 | Mann et al. |
| 5,176,644 | A | 1/1993 | Srisathapat et al. |
| 5,205,820 | A | 4/1993 | Kriesel |
| 5,207,666 | A | 5/1993 | Idriss et al. |
| 5,236,689 | A | 8/1993 | Wong et al. |
| 5,242,406 | A | 9/1993 | Gross et al. |
| 5,304,153 | A | 4/1994 | Tsujikawa |
| 5,336,194 | A | 8/1994 | Polaschegg et al. |
| 5,667,504 | A | 9/1997 | Baumann et al. |
| 5,716,343 | A | 2/1998 | Kriesel et al. |
| 5,722,957 | A | 3/1998 | Steinbach |
| 5,758,667 | A | 6/1998 | Slettenmark et al. |
| 5,766,150 | A | 6/1998 | Langkau |
| 5,769,823 | A * | 6/1998 | Otto .............................. 604/141 |
| 5,776,103 | A | 7/1998 | Kriesel et al. |
| 5,785,688 | A | 7/1998 | Joshi et al. |
| 5,792,104 | A | 8/1998 | Speckman et al. |
| 5,814,019 | A | 9/1998 | Steinbach et al. |
| 5,836,915 | A | 11/1998 | Steinbach et al. |
| 5,840,063 | A | 11/1998 | Flaherty |
| 5,895,428 | A | 4/1999 | Berry |
| 5,906,597 | A | 5/1999 | McPhee |
| 5,976,109 | A | 11/1999 | Heruth |
| 6,086,555 | A | 7/2000 | Eliasen et al. |
| 6,179,806 | B1 | 1/2001 | Sansoucy |
| 6,280,416 | B1 | 8/2001 | Van Antwerp et al. |
| 6,283,944 | B1 | 9/2001 | McMullen et al. |
| 6,554,822 | B1 | 4/2003 | Holschneider et al. |
| 6,620,151 | B2 | 9/2003 | Blischak et al. |
| 6,652,510 | B2 | 11/2003 | Lord et al. |
| 6,730,060 | B1 | 5/2004 | Steinbach et al. |
| 6,764,472 | B1 | 7/2004 | Burke et al. |
| 6,796,956 | B2 | 9/2004 | Hartlaub et al. |
| 6,805,693 | B2 | 10/2004 | Gray et al. |
| 6,902,544 | B2 | 6/2005 | Ludin et al. |
| 6,932,114 | B2 | 8/2005 | Sparks |
| 7,044,932 | B2 | 5/2006 | Borchard et al. |
| 7,083,593 | B2 | 8/2006 | Stultz |
| 7,108,686 | B2 | 9/2006 | Burke et al. |
| 7,150,741 | B2 | 12/2006 | Erickson et al. |
| 7,214,221 | B2 | 5/2007 | Fentress et al. |
| 7,367,968 | B2 | 5/2008 | Rosenberg et al. |
| 2002/0151875 | A1 | 10/2002 | Haller |
| 2002/0156361 | A1 | 10/2002 | Popowski et al. |
| 2002/0156462 | A1 | 10/2002 | Stultz |
| 2003/0175149 | A1 | 9/2003 | Searles et al. |
| 2003/0199813 | A1 | 10/2003 | Struble |
| 2004/0078000 | A1 | 4/2004 | Borchard et al. |
| 2004/0143242 | A1 | 7/2004 | Ludin et al. |
| 2005/0070875 | A1 | 3/2005 | Kulessa |
| 2005/0113745 | A1 | 5/2005 | Stultz |
| 2005/0273082 | A1 | 12/2005 | Olsen |
| 2005/0277912 | A1 | 12/2005 | John |
| 2006/0089619 | A1 | 4/2006 | Ginggen |
| 2006/0271021 | A1 | 11/2006 | Steinbach |
| 2006/0271022 | A1 | 11/2006 | Steinbach et al. |
| 2007/0185470 | A1 | 8/2007 | Steinbach et al. |
| 2007/0185740 | A1 | 8/2007 | Hooglander |

FOREIGN PATENT DOCUMENTS

| | | |
|---|---|---|
| WO | 03/068049 | 8/2003 |
| WO | 2005007223 | 1/2005 |
| WO | 2005044343 | 5/2005 |
| WO | 2005079885 | 9/2005 |

OTHER PUBLICATIONS

Karas, Beverly Schambura, "Refilling an implanatable pump", Nov. 1995.

Institute for Safe Medication practices, "Template for disaster? Fatal Injection into Wrong Port of Implanted Infusion Pump", Jan. 15, 2004.

Medtronic Educational Brief, "Pump Refill Techniques" ISOMED Pump Systems, Aug. 2003.

International Search Report, PCT/US07/01828.

International Search Report, PCT/US06/20135.

Supplementary Partial European Search Report, EP 07716956, mailed Aug. 8, 2009.

* cited by examiner

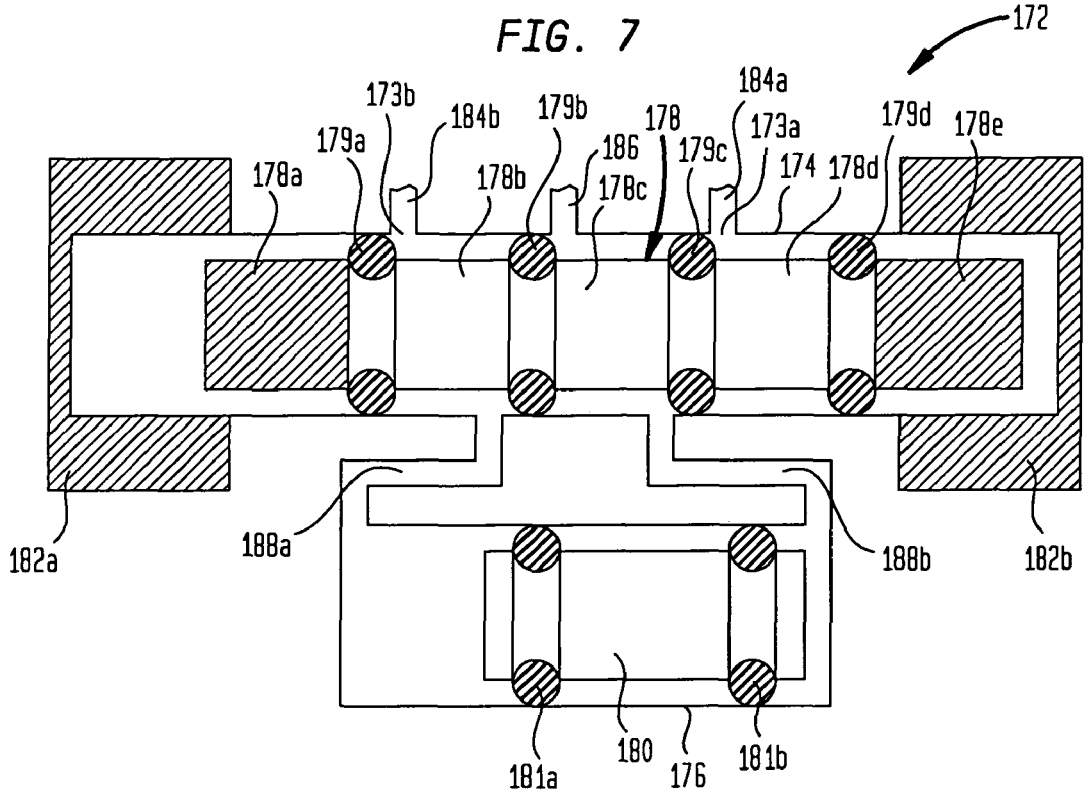
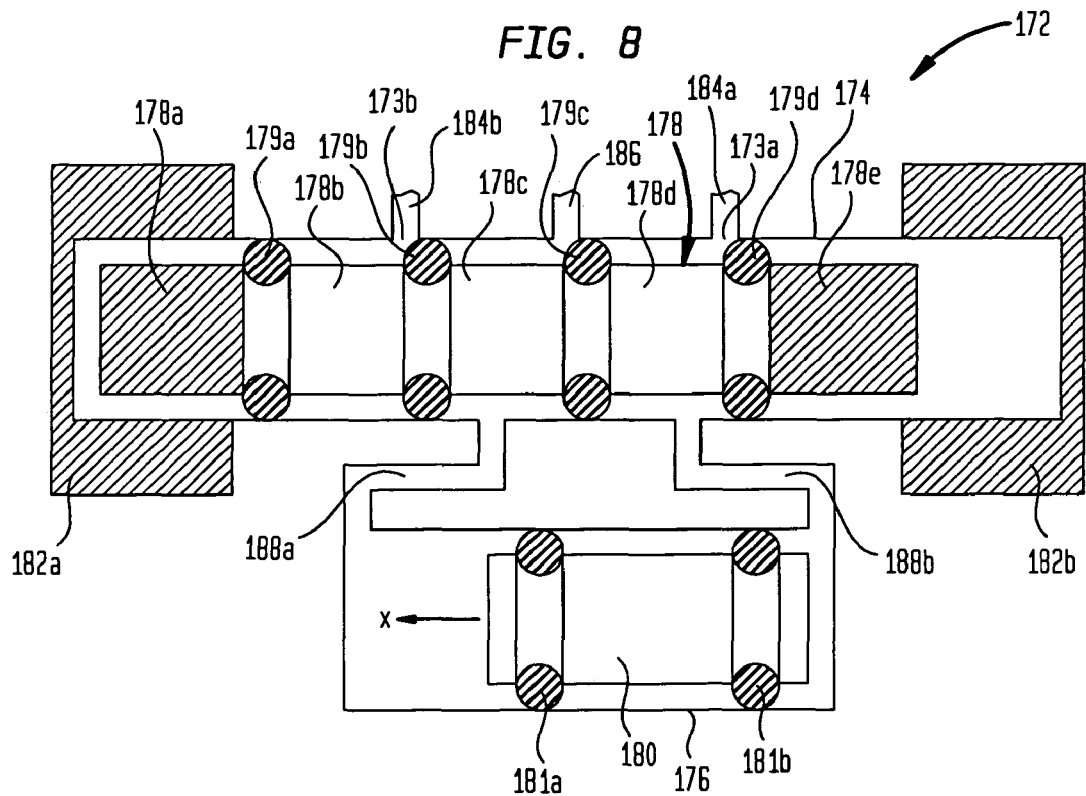

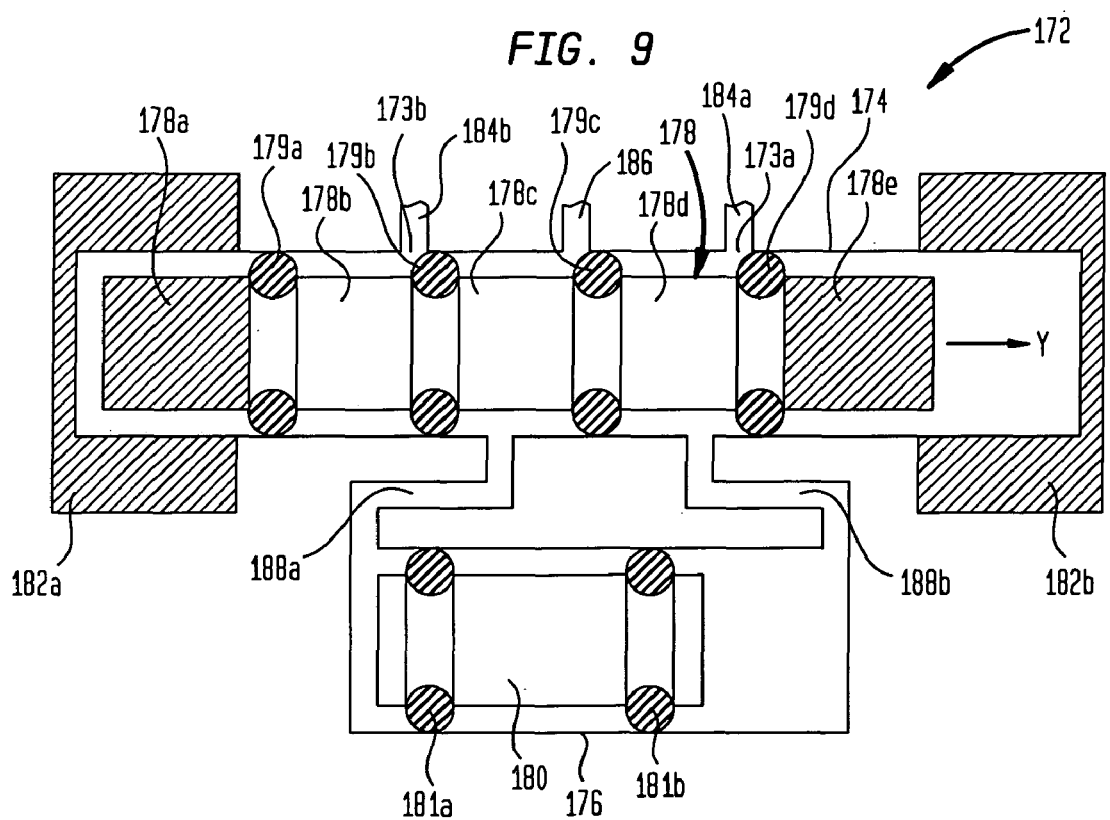
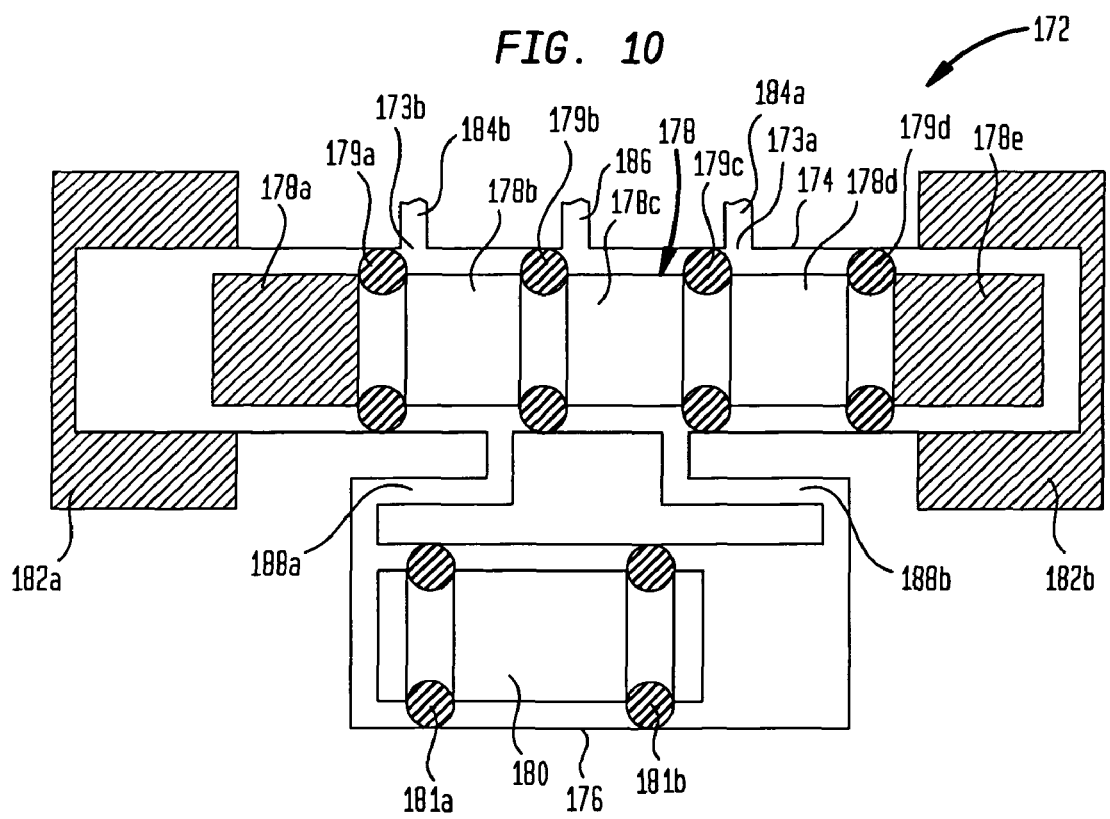

MULTI-RESERVOIR IMPLANTABLE PUMP WITH VARIABLE FLOW RATE CAPABILITIES

BACKGROUND OF THE INVENTION

The present invention relates to implantable devices, and more particularly to a multiple reservoir implantable pump that may be designed to allow different constant flow rates and bolus injection capability.

Implantable pumps have been well known and widely utilized for many years. Typically, pumps of this type are implanted into patients who require the delivery of active substances or medication fluids to specific areas of their body. For example, patients that are experiencing severe pain may require painkillers daily or multiple times per day. Absent the use of an implantable pump or the like, a patient of this type would be subjected to one or more painful injections of such medication fluids. In the case of pain associated with more remote areas of the body, such as the spine, these injections may be extremely difficult to administer and particularly painful for the patient. Furthermore, attempting to treat conditions such as this through oral or intravascular administration of medication often requires higher doses of medication and may cause severe side effects. Therefore, it is widely recognized that utilizing an implantable pump may be beneficial to both a patient and the treating physician.

Many implantable pump designs have been proposed. For example, U.S. Pat. No. 4,969,873 ("the '873 patent"), the disclosure of which is hereby incorporated by reference herein, teaches one such design. The '873 is an example of a constant flow pump, which typically include a housing having two chambers, a first chamber for holding the specific medication fluid to be administered and a second chamber for holding a propellant. A flexible membrane may separate the two chambers such that expansion of the propellant in the second chamber pushes the medication fluid out of the first chamber. This type of pump also typically includes an outlet opening connected to a catheter for directing the medication fluid to the desired area of the body, a replenishment opening for allowing for refilling of medication fluid into the first chamber and a bolus opening for allowing the direct introduction of a substance through the catheter without introduction into the first chamber. Both the replenishment opening and the bolus opening are typically covered by a septum that allows a needle or similar device to be passed through it, but properly seals the openings upon removal of the needle. As pumps of this type provide a constant flow of medication fluid to the specific area of the body, they must be refilled periodically with a proper concentration of medication fluid suited for extended release.

Implantable pumps may also be of the programmable type. Pumps of this type provide variable : flow rates, typically through the use of a solenoid pump or a peristaltic pump. In the solenoid pump, the flow rate of medication fluid can be controlled by changing the stroke rate of the pump. In the peristaltic pump, the flow rate can be controlled by changing the roller velocity of the pump. However, both of these types of programmable pumps require intricate designs and complicated controlling mechanisms. As such, it is more desirable to utilize pumps having designs similar to the aforementioned constant flow pumps.

Nonetheless, the benefit of providing a variable flow rate pump, or at least a pump having the capability of multiple fixed flow rates, cannot be forgotten. While a constant flow of medication such as a painkiller may indeed be useful in dulling chronic pain, there may be times when a patient may require additional pain relief. With a constant flow pump, the flow rate is fixed, so the physician or medical professional may only provide such relief by direct injections of painkillers and the like through the aforementioned bolus port (which provides direct access to the afflicted area), or by increasing the overall active substance concentration of the fluid housed in the pump. While indeed useful, the former amounts to nothing more than additional injections, something the pump is designed to circumvent. In addition, the latter may be considered less convenient for the physician or medical professional, since it requires choosing a different concentration of medicine, rather than merely adjusting the flow rate of the already present medication via an external programmer, as would be done with a programmable pump.

In addition, pumps are known that normally act in a fashion similar to the aforementioned constant flow type pumps, but that also allow for a patient controlled bolus dose. These pump types are sometimes referred to as Patient Controlled Actuation ("PCA") pumps. One example of such a pump is disclosed in U.S. Pat. No. 6,283,944, the disclosure of which is hereby incorporated by reference herein. During periods of regular pain or the like, PCA pumps provide a constant flow rate of medication fluid to a patient. However, during periods of heightened pain, a PCA pump may be actuated by a patient to provide an additional medication injection. Essentially, this allows for a bolus injection, in line with that described above, without the need for the use of a needle or syringe. PCA pumps also typically include a safety mechanism for preventing a patient from overdosing themselves. While such designs may be beneficial in light of standard constant flow type implantable pumps, nevertheless, such designs are often complicated and bulky.

Therefore, there exists a need for an implantable constant flow pump, which allows for multiple fixed flow rates and may be configured to allow for patient controlled bolus doses or the like.

SUMMARY OF THE INVENTION

A first aspect of the present invention is an implantable device for dispensing an active substance to a patient. A first embodiment of this first aspect includes a propellant chamber defined by a first flexible membrane and a second flexible membrane, a first active substance chamber separated from the propellant chamber by the first flexible membrane, and a second active substance chamber separated from the propellant chamber by the second flexible membrane. The implantable device may further include an outlet in fluid communication with the first and second active substance chambers, and a resistor in communication between each of the chambers and the outlet. The implantable device may also include first and second replenishment openings for refilling the first and second chambers. These openings may be offset from the chambers so as to allow for the height of the device to be reduced. The implantable device is preferably capable of housing two different active substances in the chambers.

A second embodiment of this first aspect is an implantable pump. The implantable pump of this embodiment includes a housing defining at least three chambers and an outlet in fluid communication with at least two of the chambers. One of the chambers is juxtaposed between two flexible membranes and contains a propellant capable of expanding isobarically.

A second aspect of the present invention is a method of providing different constant flow rates of an active substance to a patient. The method in accordance with this second aspect includes the steps of providing an implantable device having at least first and second active substance chambers and filling at least one of the first and second chambers or both of the chambers with the active substance in order to provide a selected flow rate of the active substance to the patient. Filling only the first chamber with the active substance preferably provides a first flow rate of the active substance, filling only the second chamber with the active substance preferably provides a second flow rate of the active substance, and filling both the first and second chambers with the active substance preferably provides a third flow rate of the active substance.

A third aspect of the present invention is an implantable pump with patient controlled actuation capabilities. The pump in accordance with this third aspect preferably includes a housing defining at least a first, second and third chamber, an outlet in fluid communication with the first chamber, and a patient controlled actuation mechanism in fluid communication with the second chamber. The third chamber is preferably juxtaposed between two flexible membranes. The third chamber may house a propellant capable of expanding isobarically, thereby causing fluid contained within the first and second chambers to be dispelled therefrom. The patient controlled actuation mechanism includes a valve assembly is preferably capable of being actuated by the patient, where selective operation of the valve assembly is accomplished by one or more magnets. The valve assembly may further include a first cylinder housing a first piston, and a second cylinder housing a second piston, where displacement of the first piston causes actuation of a dose of an active substance to a patient. The pump may also include means for selectively actuating the one or more magnets and means for preventing over medication of a patient

BRIEF DESCRIPTION OF THE DRAWINGS

A more complete appreciation of the subject matter of the present invention and the various advantages thereof can be realized by reference to the following detailed description in which reference is made to the accompanying drawings in which:

FIG. 7 is an enlarged cross section view of the valve assembly shown in FIG. 5, in a first position.

FIG. 8 is an enlarged cross section view of the valve assembly shown in FIG. 5, in a second position.

FIG. 9 is an enlarged cross section view of the valve assembly shown in FIG. 5, in a third position.

FIG. 10 is an enlarged cross section view of the valve assembly shown in FIG. 5, in a fourth position.

DETAILED DESCRIPTION

In describing the preferred embodiments of the subject matter illustrated and to be described with respect to the drawings, specific terminology will be used for the sake of clarity. However, the invention is not intended to be limited to any specific terms used herein, and it is to be understood that each specific term includes all technical equivalents which operate in a similar manner to accomplish a similar purpose.

Figure 1:
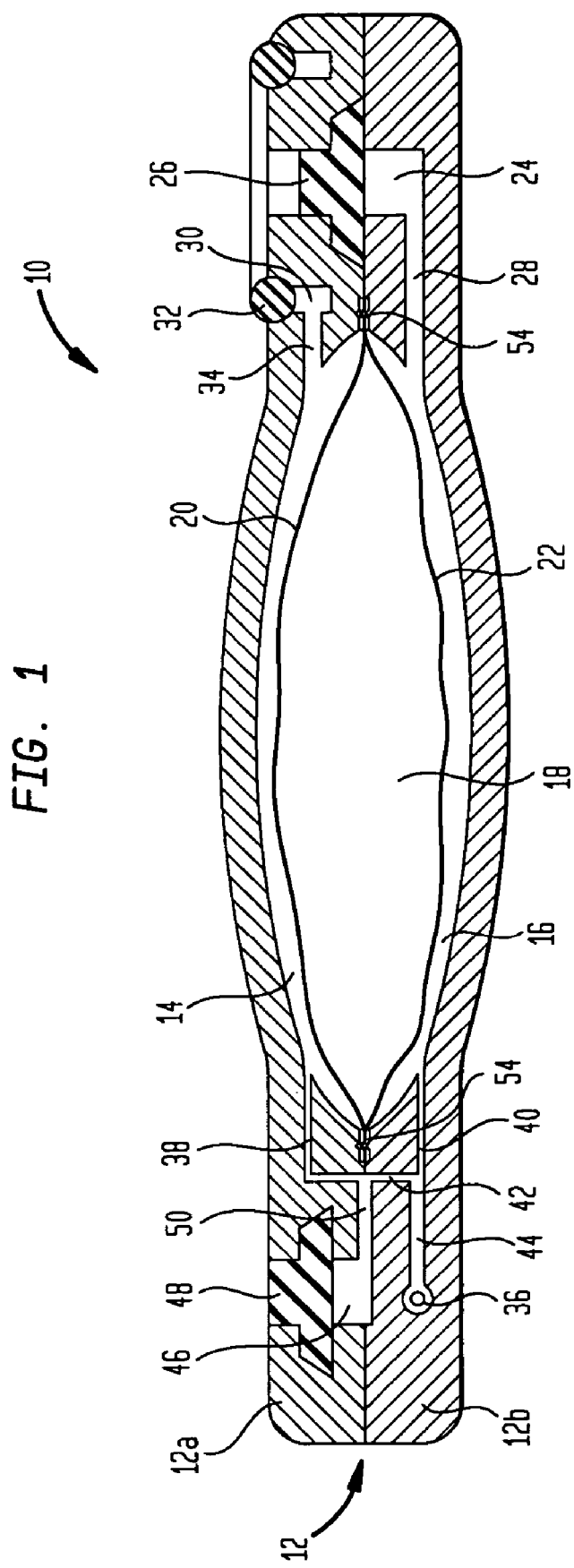
FIG. 1 is a cross sectional front view of an implantable pump in accordance with an embodiment of the present invention.
Figure 2:
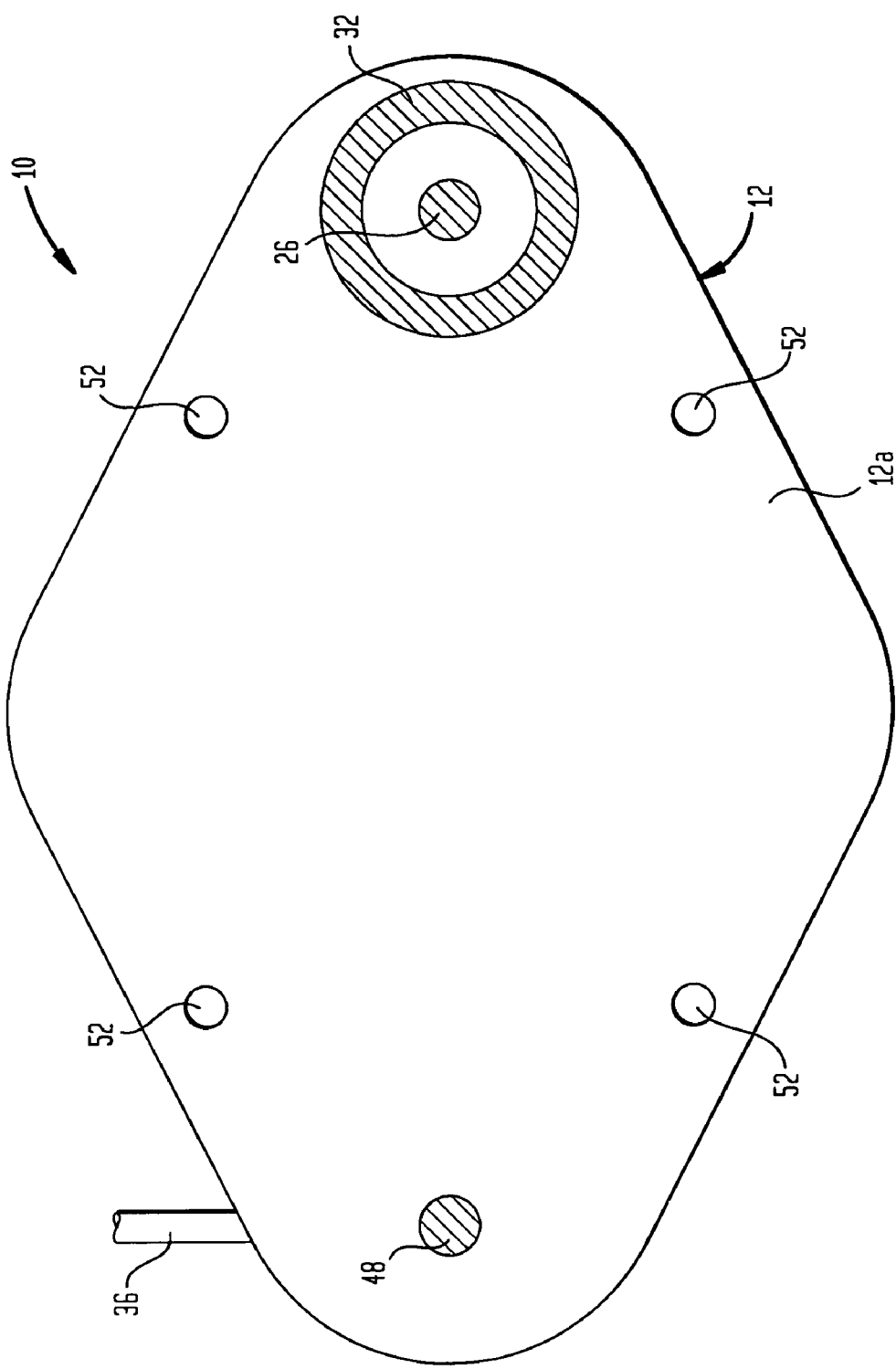
FIG. 2 is a top view of the implantable pump shown in FIG. 1.

Referring to the drawings, wherein like reference numerals refer to like elements, there is shown in FIGS. 1 and 2, in accordance with various embodiments of the present invention, an implantable pump designated generally by reference numeral 10. In a preferred embodiment, pump 10 is a constant flow pump including a housing 12, which defines an interior having three reservoirs or chambers 14, 16 and 18. As best shown in FIG. 1, chamber 18 is preferably formed between two flexible membranes 20 and 22, while chamber 14 is formed between a top portion 12a of housing 12 and membrane 20, and chamber 16 is formed between a bottom portion 12b of housing 12 and membrane 22. It is noted that flexible membranes 20 and 22 may be of any design known in the art, for example, a membrane like that disclosed in commonly owned U.S. Pat. No. 5,814,019, the disclosure of which is hereby incorporated by reference herein. In a preferred embodiment, chambers 14 and 16 are designed and configured to receive and house active substances such as medication fluids for the relief of pain, treatment of spasticity and neuro-mechanical deficiencies and the administration of chemotherapy, while chamber 18 is preferably designed and configured to contain a propellant which expands isobarically under constant body heat. This expansion necessarily displaces membranes 20 and 22, towards top portion 12a and bottom portion 12b respectively, so as to expel any active substances contained within chambers 14 and 16. This will be discussed more fully below.

Pump 10 further includes a first replenishment port 24 formed in housing 12. Essentially, first replenishment port 24 is an opening formed in both top portion 12a and bottom portion 12b of housing 12. This port is preferably covered by a first septum 26, which is capable of being pierced by an injection needle and, upon removal of such needle, is capable of automatically resealing itself. Septa of this type are well known to those of ordinary skill in the art. As pump 10 is designed to medicate a patient over a limited period of time, first replenishment port 24 is utilized for replenishing chamber 16 when empty or near empty. As shown in FIG. 1, port 24 is connected to chamber 16 by a first passage 28. In addition, housing 12 preferably includes a second, replenishment port 30 for replenishing chamber 14 with an active substance or the like, through the connection formed by second passage 34. Similar to first replenishment port 24, second replenishment port 30 is covered by a second, septum 32. However, as shown in FIGS. 1 and 2, port 30 and septum 32 are ring shaped, so that they extend around port 24. This design allows for both replenishment ports to be located in a relatively small area without requiring the need for a larger housing 12.

During a replenishment procedure, a physician and/or other medical professional typically inserts an injection needle into an area of a patient's body where pump 10 is located, such that it may pierce one of first septum 26 or second septum 32. Thereafter, operation of the needle causes injection of solution from the needle to pass into either chamber 14 through passage 34 or chamber 16 through passage 28. It is noted that the particular dimension of pump 10 and/or the patient's need may require such a process to be repeated at given intervals, for example, monthly, weekly, etc. In addition, as will be more fully discussed below, the replenishment process may be performed so as to vary the particular flow rate of a medication fluid to the patient. Pump 10, as shown in FIG. 1, also includes an outlet catheter 36 for remote delivery of a fluid contained within chambers 14 or 16 to a specific location within the body of a patient. Catheter 36 may be any well known catheter suitable for directing a medication fluid or the like to a location away from pump 10. For example, catheter 36 may direct medication fluid from a pump implanted at or near the surface of a patient's body to the spinal or other remote area. In the embodiment shown in FIG. 1, catheter 36 is in fluid communication with both chambers 14 and 16 through a series of connected passages. Specifically a first flow resistor 38 is connected to chamber 14, while a second flow resistor 40 is connected to chamber 16. It is noted that both resistors 38 and 40 may be any fluid resistor known in the art. In their most simplistic form, resistors 38 and 40 are essentially narrow tubes or capillaries which are dimensioned so as to allow a maximum flow rate therethrough. Thus, regardless of the flow rate of fluid from either chamber 14 or 16, resistors 38 and 40 act as restrictors and govern the maximum rate. Resistors 38 and 40 are preferably connected to a collecting duct 42, which is in turn connected to a tube or capillary 44 in communication with catheter 36.

In operation, expansion of propellant housed within chamber 18 exerts a force upon membranes 20 and 22. This force displaces membranes 20 and 22, towards top portion 12a and bottom portion 12b respectively, which in turn necessarily expels fluid contained in chambers 14 and 16 through resistors 38 and 40 respectively and ultimately out catheter 36. The flow rate which was determined by resistors 38 and 40 determines the flow rate of the fluid through and out of catheter 36.

In addition to the aforementioned first and second replenishment ports 24 and 30, pump 10 also preferably includes a bolus port 46 covered by a bolus septum 48. Essentially, this bolus port allows for direct introduction of a solution into outlet catheter 36 and to the specific target area of the body. This port is particularly useful when a patient requires additional or stronger medication, such as a single bolus injection, and/or when it is desired to test the flow path of catheter 36. Such an injection is performed in a similar fashion to the above discussed injection in replenishment ports 24 and 30. As shown in FIG. 1, fluid injected into bolus port 46 passes through bolus passage 50 and into collecting duct 42. Thereafter, similar to above, such fluid passes through tube 44 and out catheter 36. Thus, an injection into bolus port 46 bypasses resistors 38 and 40, and thus provides direct access to catheter 36, without any reduction in flow rate. It is also possible to utilize bolus port 46 to withdraw fluid from the body. For example, where pump 10 is situated within the body such that catheter 36 extends to the vertebral portion of the spinal column, a needle with a syringe connected thereto may be inserted into bolus port 46 and operated to pull spinal fluid through catheter 3 and into the syringe.

The design of pump 10 preferably allows for the selective administration of any fluid housed therein, at up to three different flow rates. As discussed above, upon the expansion of a propellant housed within chamber 18, any fluid housed within chambers 14 and 16 is ultimately expelled through catheter 36. The aforementioned resistors 38 and 40 dictate the maximum flow rate for any fluid being expelled from chambers 14 and 16 respectively. In certain preferred embodiments, these resistors differ in the maximum flow rate for which they allow. Thus, depending upon which chamber(s) is filled/injected with fluid, the flow rate through catheter 36 will preferably vary. For example, if chamber 14 is filled with a fluid, and chamber 16 is empty, the overall flow rate of fluid from pump 10 is determined by resistor 38. Alternatively, if chamber 16 is filled with a fluid, and chamber 14 is empty, the overall flow rate of fluid from pump 10 is determined by resistor 40. If both chambers 14 and 16 are filled with a fluid, the highest flow rate occurs and is determined by the combination of the flow rates dictated by resistors 38 and 40. Clearly, this three flow rate capability is beneficial in varying the flow rate of a medication fluid or the like depending upon the particular needs of a patient.

It is noted that regardless of the amount of fluid being housed in either chambers 14 or 16, or both, the pressure being exerted on membranes 20 and 22 by expanding propellant housed in chamber 18 is sufficient for expelling the fluid therefrom. Thus, pump 10 is designed so that propellant contained in chamber 18 expands and exerts a force strong enough to always push fluid from chambers 14 and 16. In turn, resistors 38 and 40 are designed to reduce this initial flow rate from chambers 14 and 16, so that regardless of the force being applied to membranes 20 and 22, by the propellant, a constant flow rate of fluid into collection duct 42 may be seen. In other words, pump 10 is designed so that the minimum flow rate of fluid directly from chambers 14 and 16 should always be greater than the flow rate of the same fluid through resistors 38 and 40. This ensures that a predetermined constant flow of fluid will occur regardless of the overall amount of fluid contained in chambers 14 and 16.

In operation, a doctor and/or other medical professional may easily utilize pump 10 so as to provide three different flow rates of medication to a patient. Initially, pump 10 may be implanted into the body of a patient by well known methods for implanting such implantable devices. As shown in FIG. 2, suture holes 52 may be useful in attaching pump 10 to a specific portion of the body so that catheter may be directed to the portion which requires the medication fluid or the like. In certain preferred embodiments, pump 10 includes four suture holes 52 that each extend through housing 12 from top portion 12a to bottom portion 12b, and that may be utilized in conjunction with sutures or the like. Once pump 10 is implanted in the body of a patient, the aforementioned medical professional may essentially pick and choose which chambers to fill. As set forth above, filling of either chamber 14 or chamber 16 may provide either a first or second flow rate of fluid, while filling both may provide a third flow rate. Depending upon the particular conditions of the patient (e.g.—the patient's current level of pain), the medical professional may determine what chambers to fill and/or leave empty. In combination with the aforementioned direct bolus injection capability, this three flow design is clearly beneficial to both a patient and medical professional. As pump 10 is designed to house a limited amount of medication fluid, it must be refilled regularly. A doctor or nurse may utilize the regularly scheduled replenishment procedure as an opportunity to further monitor the patient and determine the proper flow rate for treating the patient's infirmity. Thus, if a doctor determines that the patient requires more medication fluid to be directed to the afflicted area, he/she may simply fill both chambers, or the single chamber associated with the faster flow rate resistor. Alternatively, when less medication is desired, only one chamber or the chamber associated with the slower resistor may be filled. While allowing multiple flow rates, the design of the present dual reservoir constant flow pump 10 is an improvement upon complicated programmable pumps, as the present invention merely requires simple injections, or lack there of, to refill the correct chambers, rather than the operation of complicated mechanisms or electronics. As is clearly recognized by those of ordinary skill in the art, these replenishing injections are something that are required in the proper operation of all pumps, regardless of their type.

In addition to the varying flow rate discussed above, the design of pump 10 also allows for the administration of up to two different active substances, or a combination of both, from a single pump. Clearly, the dual reservoir design of pump 10 as shown in FIGS. 1 and 2 may allow for two different medication fluids or the like to be housed in chambers 14 and 16. Thereafter, upon the expansion of a propellant housed within chamber 18, either one or both (depending on which chambers have been filled) may be administered to a patient.

Figure 3:
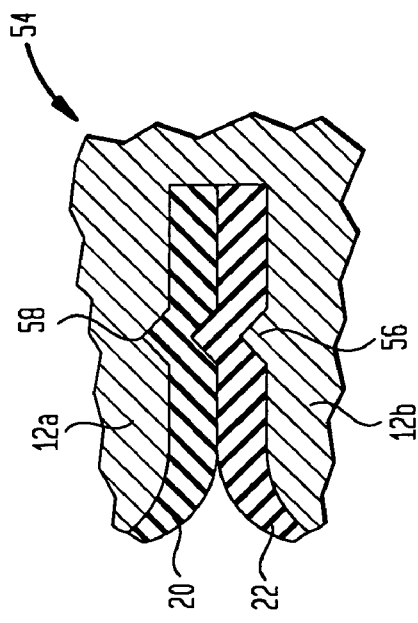
FIG. 3 is an enlarged view of an attachment area of the pump shown in FIG. 1.

As the various ports 24, 30 and 36 of pump 10 (as well as their respective septa 26, 32, 38) are located to the side, and are not located above chambers 14, 16 and 18, housing 12 is of low profile and may be comprised of only the aforementioned top and bottom portions 12a and 12b simply affixed together by any well known means, such as adhesive, welding, screw cooperation, snap fitting and the like. Top and bottom portions 12a and 12b preferably cooperate so as to capture and retain membranes 20 and 22 therebetween. As shown in FIG. 1 and the more detailed exploded view of FIG. 3, top and bottom portions 12a and 12b preferably form an attachment area 54 for achieving this capturing and retaining of the membranes. Attachment area 54 preferably includes a projection 56 located bottom portion 12b and a depression 58 located on top portion 12a. During assembly, top and bottom portions 12a and 12b are sandwiched together, with membranes 20 and 22 therebetween. This sandwiching step necessarily causes projection 56 to be forced into depression 58. Similarly, a portion of each membrane 20 and 22 is also forced into depression 58 by projection 56. Thus, a crimp-like connection is formed, thereby capturing and retaining membranes 20 and 22 between top and bottom portions 12a and 12b. It is noted that other configurations for attachment area 54 are envisioned, as would be apparent to those of ordinary skill in the art.

Figure 4:
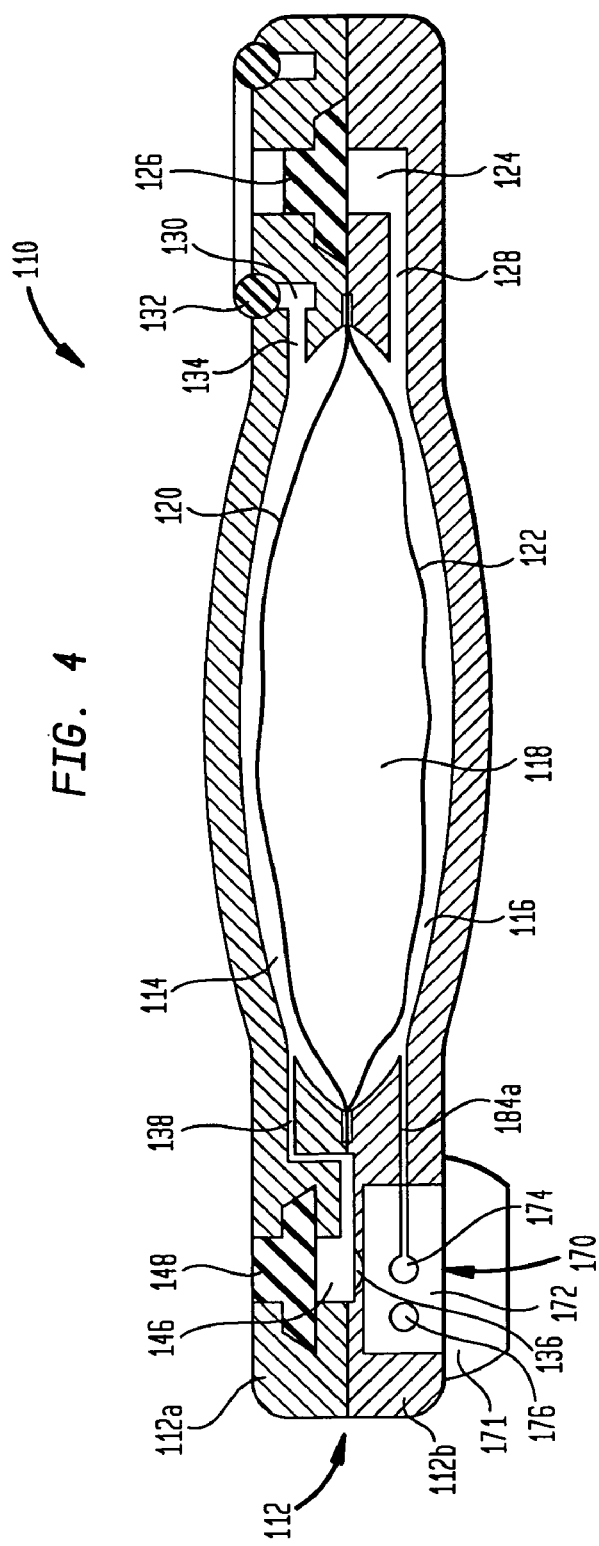
FIG. 4 is a cross sectional front view of an implantable pump in accordance with another embodiment of the present invention.
Figure 5:
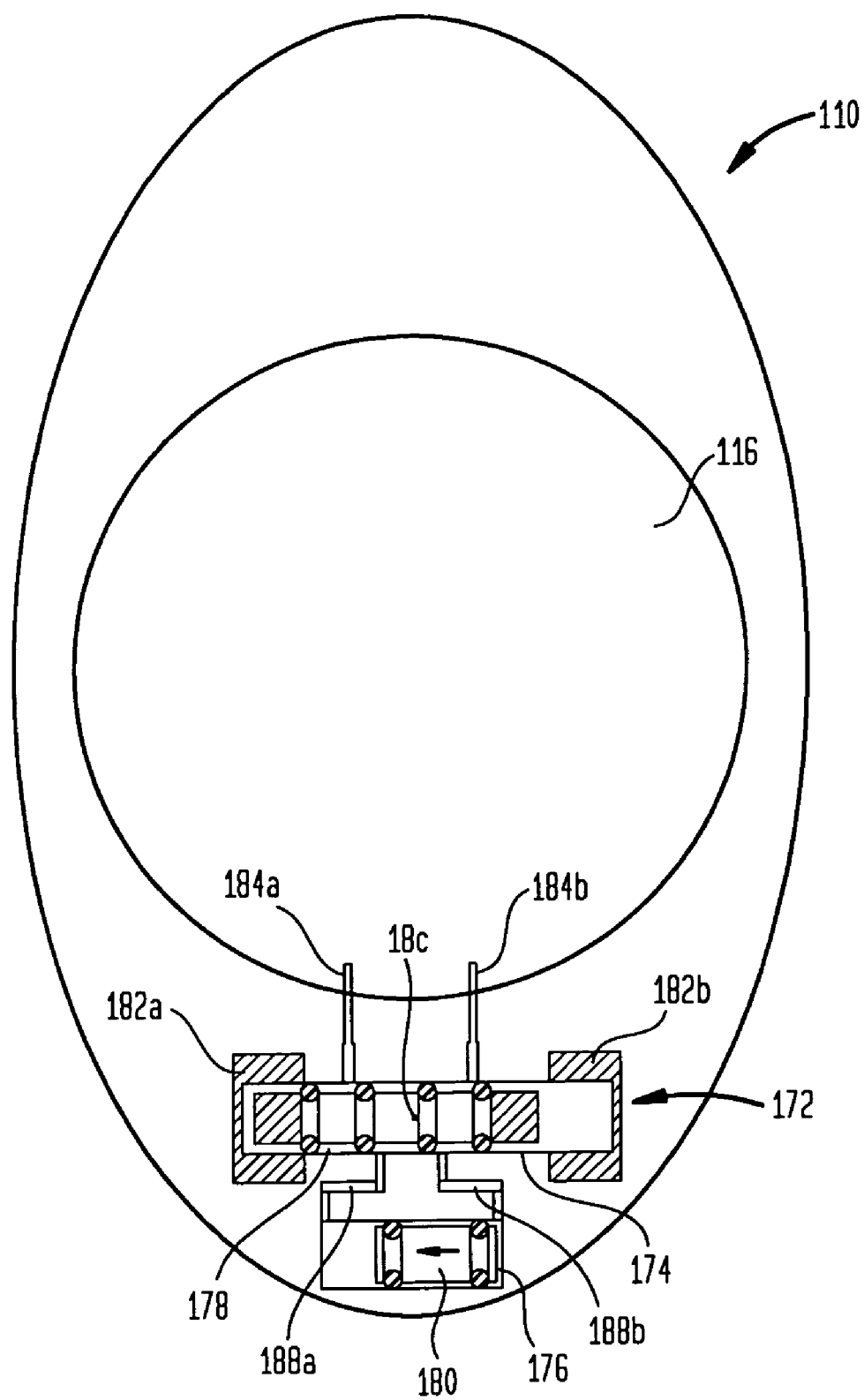
FIG. 5 is a cross sectional bottom view of the implantable pump shown in FIG. 4, showing a valve assembly therein.
Figure 6:
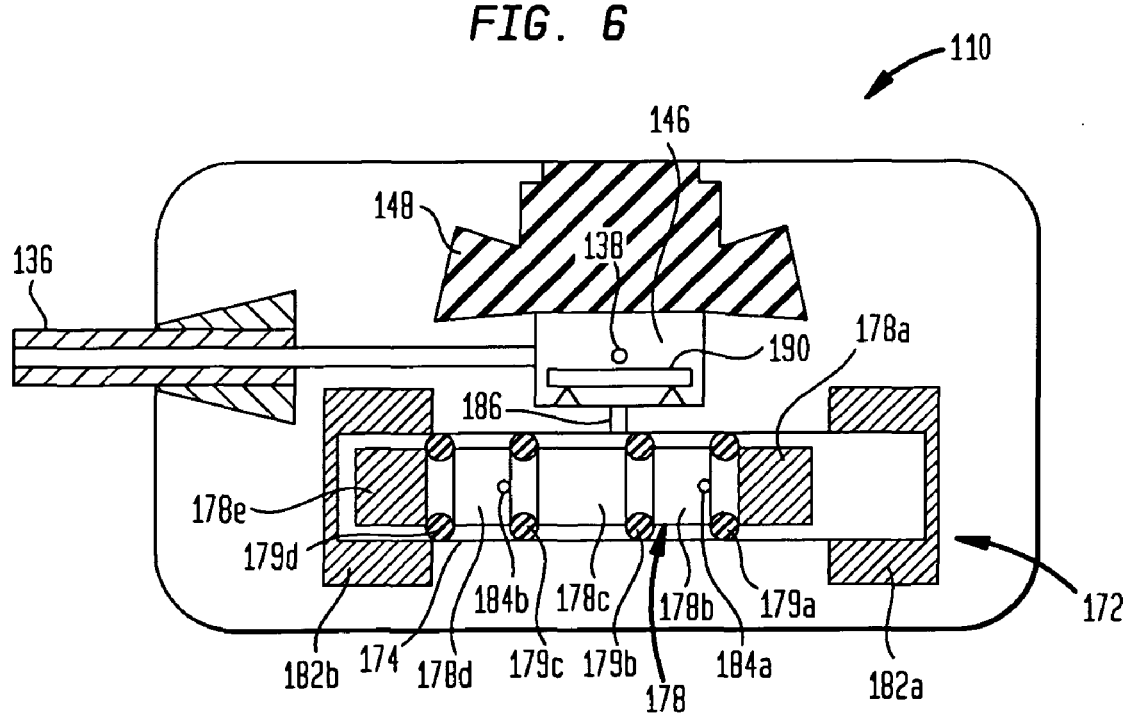
FIG. 6 is a cross sectional left side view of the implantable pump shown in FIG. 4, showing a valve assembly therein.

In accordance with the present invention, another embodiment implantable pump 110 is depicted in FIGS. 4-6. It is noted that pump 110 operates in a similar fashion to that of the above described pump 10. As such, like elements of pump 110 are labeled with similar reference numerals, but within the 100 series of numbers. For example, the two membranes of pump 110 are similar to the above described membranes 20 and 22, and as such, are labeled as 120 and 122. Rather than being a pump with the above described three constant flow rate capability, pump 110 is designed to be a constant flow rate pump with patient controlled actuation capabilities. Essentially, chamber 114 is utilized to provide a constant flow of fluid to catheter 136, in substantially the same manner as described above with regard to chamber 14 of pump 10. However, in this second embodiment, chamber 116 is utilized for providing fluid to a patient controlled actuation assembly, which will be discussed more fully below.

As briefly mentioned above, fluid expelled from chamber 114 passes through a constant flow resistor 138, through bolus port 146, to catheter 136. This is similar to the above discussed operation of chamber 14 of pump 10, and is shown in both FIGS. 4 and 6. In this embodiment however, fluid housed within chamber 116 passes through channels 184a and 184b to an electronic patient controlled actuation unit 170 capable of allowing for patient controlled bolus doses to be administered in a manner to be further described. Unit 170 includes an electronic unit 171, and a valve assembly 172 having a first cylinder 174 and a second cylinder 176, which will be discussed further below in connection with FIGS. 7-10. Finally, in a similar fashion to bolus port 46 of pump 10, pump 110 also includes a bolus port 146 for allowing direct access to catheter 136.

Valve assembly 172 is more particularly shown in the enlarged and more detailed views of FIGS. 5-10. As noted above, assembly 172 comprises a first cylinder 174 and a second cylinder 176, which house first and second pistons 178 and 180 respectively. First piston 178 further includes five piston sections 178a, 178b, 178c, 178d and 178e separated by four o-rings 179a, 179b, 179c and 179d. As depicted in FIGS. 7-10, piston sections 178a and 178e are adapted to be attracted by electrical forces or the like. For example, piston sections 178a and 178e may be a metallic material that may be attracted by magnets or coils 182a and 182b encompassing the ends of first cylinder 174. Piston sections 178b, 178c and 178d are dimensioned so as to have an outside diameter which are smaller than the inside diameter of first cylinder 174. Thus, fluid may pass through a channel or circular opening formed between the piston sections and the cylinder. The aforementioned o-rings 179a-d define these piston sections and also seal the channels or openings formed by each section and first cylinder 174 from each other. In a similar fashion, piston 180 includes two o-rings 181a and 181b for sealing the piston against second cylinder 176. However, it is noted that piston 180 is sized so as to fit more snuggly within second cylinder 176, and is not adapted to form useful channels or openings therebetween.

Valve assembly 172 further includes two openings 173a and 173b for receiving the aforementioned inlets 184a and 184b in fluid communication with chamber 116, a single outlet 186 in fluid communication with bolus port 146 and catheter 136, and two passages 188a and 188b that allow first cylinder 174 and second cylinder 176 to be in fluid communication. It is noted that the cross sectional bottom view of FIG. 5 more particularly shows the fluid communication between chamber 116 and valve assembly 172. As shown in that figure, inlets 184a and 184b essentially extend between each of those components. However, in other embodiments, a single exit from chamber 116 may be connected to openings 173a and 173b of valve assembly 172 by a Y-joint or the like. As more clearly shown in the side view of FIG. 6, outlet 186 extends between first cylinder 174 and bolus port 146. This ultimately allows for fluid dispelled from valve assembly 172 to exit through catheter 136. It is noted that outlet 186 extends in a direction which is perpendicular to inlets 184a and 184b. This is depicted in FIGS. 5 and 6, by showing the ends of these components. However, with regard to FIGS. 7-10, these components are shown in a parallel relationship for clarity purposes. Finally, as best shown in FIG. 6, bolus port 146 may include a plate 190 for preventing the inadvertent access of outlet 186 by a needle inserted into port 146.

The operation of valve assembly 172 will now be discussed in conjunction with FIGS. 7-10, which depict the sequence of movements of the various components of the valve assembly. Initially, pistons 178 and 180 are located in the positions depicted in FIG. 7. It is noted that in this position, fluid is located in the empty portion of cylinder 176 located to the left of piston 180. However, because of the cooperation of the other elements of assembly 172, no fluid is capable of being dispelled. Most notably, passage 188b is not in fluid communication with inlet 184a, and passage 188a is not in fluid communication with outlet 186. However, upon the activation of magnet 182a by the patient, section 178a of first cylinder 178 is pulled towards magnet 182a, resulting in the position shown in FIG. 8.

Subsequent to the movement of first cylinder 178, as shown in FIG. 8, inlet 184a is now in fluid communication with passage 188a, as the position of piston 178 allows for fluid to pass around piston section 178d. Thus, fluid being constantly expelled from chamber 116 is capable of flowing through inlet 184a and around piston section 178d, through passage 188a, to a position within second cylinder 176 to the right of piston 180. Upon the build up of sufficient pressure (provided by the constant flow from chamber 116), piston 180 is displaced within second cylinder 176 in the direction depicted by arrow X. This, in turn, pushes the fluid contained to the left of piston 180 through passage 188b, around piston section 178c, through outlet 186 and eventually through catheter 136 to a portion of the body of the patient in which pump 110 is implanted. Therefore, a predetermined amount of fluid is expelled from pump 110, while a substantially similar amount of fluid remains to the right of the recently displaced piston 180. This latter position is shown in FIG. 9.

With piston 180 now being situated to the left side of second cylinder 176 and fluid located within second cylinder 176 to the right side of piston 180 (as shown in FIG. 9), piston 178 may now be moved within first cylinder 174 in the direction of arrow Y, shown in FIG. 9. Once again, it is noted that this may be accomplished by activating magnet 182b. FIG. 10 depicts the position of piston 178 within first cylinder 174 after the activation of magnet 182b. This right side position now creates an open fluid passage extending through inlet 184b, around piston section 178b, through passage 188b and into second cylinder 176 to the left of piston 180. Similarly, an open fluid passage now exists from the right side of piston 180 within second cylinder 176, through passage 188a, around piston section 178c, and through outlet 186, where it may ultimately exit catheter 136. Like that described above, fluid being expelled from chamber 116 displaces piston 180 to the right, thereby expelling the fluid contained within second cylinder 176. Thus, a predetermined amount is injected into the patient's body and a similar amount is recharged into second cylinder 176 on the opposite side of piston 180. Upon completion of this step, the components of valve assembly 172 retain the position depicted in FIG. 7. Thus, the above described steps may be followed to perform more patient desired injections.

This patient actuated process may be conducted over and over again through the selective actuation of magnets or coils 182a and 182b. The only limitation to the amount of times the process may be performed is the overall amount of fluid housed within chamber 116. It is noted that actuation of magnets 182a and 182b may be accomplished through many different procedures. For example, as mentioned above, unit 170 includes an electronic unit 171 which preferably has a power source, such as a battery. This power source preferably may be selectively applied to either magnet 182a or 182b. In a simplistic form, magnets 182a and 182b may be connected to the power source through a well known electrical connection and a switch may be employed for choosing which magnet gets an electrical current applied thereto.

Further, a controlling mechanism is preferably provided for selectively applying power to the magnets. Many different such mechanisms are well known and widely utilized with implantable devices for implantation into a patient's body. For example, prior art devices have shown that it is possible to utilize dedicated hard wired controllers, infrared controllers, or the like, which controllers could be used in accordance with the present invention to control various elements. U.S. Pat. No. 6,589,205 ("the '205 patent"), the disclosure of which is hereby incorporated by reference herein, teaches the use of a wireless external control. As discussed in the '205 patent, such a wireless control signal may be provided through modulation of an RF power signal that is inductively linked with the pump. The '205 patent cites and incorporates by reference U.S. Pat. No. 5,876,425, the disclosure of which is also hereby incorporated by reference herein, to teach one such use of forward telemetry or the exchange of information and programming instructions that can be used with the present invention to control the pump and the various aforementioned elements that are varied in order to affect the flow rate. However, it is noted that similar external controllers may also be utilized. Such controllers can send control signals wirelessly (such as by IR, RF or other frequencies) or can be wired to leads that are near or on the surface of the patient's skin for sending control signals. Furthermore, a pump in accordance with the present invention may include safeguards to prevent the inadvertent signaling or improper programming of the pump. For example, the present invention could utilize a secure preamble code or encrypted signals that will be checked by software or hardware used for controlling the pump or even dedicated only for security purposes. This preamble code would prevent the inadvertent actuation of magnets 182a and 182b, from being caused by outside unrelated remote control devices or signals and by other similar pump controllers.

Preferably, an additional controller may be provided to prevent a patient from over utilizing the patient controlled actuation features. Preferably, such controller may include a digital timer (i.e. a clock) that must time out (after a preselected interval of time before the patient can actuate the magnets again. Other safety precautions may be used, such as passwords, hardware or software keys, encryption, multiple confirmation requests or sequences, etc. by the software or hardware used in the programming of the pump to prevent over-use of the patient controlled dose.

The electronics and control logic used with the present invention for control of the magnets may be located internally with or in the implantable pump and/or externally with any external programmer device used to transmit pump programming information to control the pump. The electronics can also be used to perform various tests, checks of status, and even store information about the operation of the pump or other physiological information sensed by various transducers.

An external programmer device may also be avoided by incorporating the necessary logic and electronics in or near or in the implantable pump such that control can be accomplished, for example, via control buttons or switches or the like that can be disposed on or below the surface of the skin. Of course, necessary precautions (such as confirmation button pressing routines) would need to be taken so that inadvertent changing of programming is again avoided.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable device for dispensing an active substance to a patient comprising:
a propellant chamber defined by a first flexible membrane and a second flexible membrane, the first and second flexible membranes attached to each other to entirely surround the propellant chamber;
a first active substance chamber separated from said propellant chamber by the first flexible membrane;
a second active substance chamber separated from said propellant chamber by the second flexible membrane;
an outlet in fluid communication with said first and second active substance chambers;
a first replenishment opening in fluid communication with said first active substance chamber and a first septum sealing the first replenishment opening; and a second replenishment opening in fluid communication with said second active substance chamber and a second septum sealing the second replenishment opening.

2. The implantable device according to claim 1, further comprising a first resistor in fluid communication between said first active substance chamber and said outlet, and a second resistor in fluid communication between said second active substance chamber and said outlet.

3. The implantable device according to claim 1, further comprising a bolus port in fluid communication with said outlet, and a bolus septum sealing the bolus port.

4. The implantable device according to claim 1, wherein said first and second replenishment openings are offset from said chambers.

5. The implantable device according to claim 1, wherein said propellant chamber contains a propellant capable of expanding isobarically, the propellant cooperating with the first and second flexible membranes to reduce the volume of said first and second active substance chambers upon expansion of the propellant.

6. The implantable device according to claim 1, further comprising a plurality of suture holes for attaching said device to said patient.

7. The implantable device according to claim 1, wherein said first and second active substance chambers are filled with the same active substance.

8. The implantable device according to claim 1, wherein said first active substance chamber is filled with a first active substance and said second active substance chamber is filled with a second active substance.

9. An implantable pump comprising:
a housing and two flexible membranes disposed within said housing, said housing and said two flexible membranes defining at least first, second, and third chambers, said housing further including a first replenishment opening fluid communication with said first chamber and a first septum sealing first replenishment opening, and a second replenishment opening in fluid communication with said second chamber and a second septum sealing the second replenishment opening; and
an outlet in fluid communication with at least said first and second chambers,
wherein said two flexible membranes are attached to each other to entirely surround said third chamber and said third chamber contains a propellant capable of expanding isobarically.

10. The implantable pump according to claim 9, further comprising first and second resistors, said first resistor in fluid communication between said outlet and said first chamber and said second resistor in fluid communication between said outlet and said second chamber.

11. The implantable pump according to claim 9, wherein said first chamber includes a first substance and said second chamber includes a second active substance.

12. The implantable pump according to claim 9, wherein said first and second replenishment openings are offset from said chambers.

13. The implantable pump according to claim 9, wherein said housing further includes a bolus opening in fluid communication with said outlet, and a bolus septum sealing the bolus opening.

14. The implantable pump according to claim 9, further comprising a plurality of suture holes for attaching said pump to a body of a patient.

15. The implantable pump according to claim 9, wherein said first and second chambers are filled with the same active substance.

16. An implantable pump comprising:
a housing having first and second portions;
a first flexible membrane captured between said first and second portions;
a second flexible membrane captured between said first and second portions;
a first chamber defined by said first portion of said housing and said first flexible membrane;
a second chamber defined by said second portion said housing and said second flexible membrane;
a third chamber defined solely by said first and second flexible membranes;
an outlet in fluid communication with said first and second chambers,
wherein said housing further includes a first replenishment opening in fluid communication with said first chamber and a first septum sealing the first replenishment opening, and a second replenishment opening in fluid communication with said second chamber and a second septum sealing the first replenishment opening.

17. The implantable pump according to claim 16, wherein said first and second chambers house active substances and said third chamber houses a propellant capable of expanding isobarically.

18. The implantable pump according to claim 17, wherein expansion of said third chamber causes the active substances contained within said first and second chambers to be dispelled therefrom.

19. The implantable pump according to claim 18, wherein said first chamber includes a first active substance and said second chamber includes a second active substance.

20. The implantable pump according to claim 16, further comprising first and second resistors, said first resistor in fluid communication between said outlet and said first chamber and said second resistor in fluid communication between said outlet and said second chamber.

21. The implantable pump according to claim 16, wherein said first chamber includes a first active substance and said second chamber includes a second active substance.

22. The implantable pump according to claim 16, wherein said first and second replenishment openings are offset from said chambers.

23. The implantable pump according to claim 16, wherein said housing further includes a bolus opening in fluid communication with said outlet, and a bolus septum sealing the bolus opening.

24. The implantable pump according to claim 16, further comprising a plurality of suture holes for attaching said pump to a body of a patient.

25. The implantable pump according to claim 16, wherein said first and second chambers are filled with the same active substance.

* * * * *

UNITED STATES PATENT AND TRADEMARK OFFICE
CERTIFICATE OF CORRECTION

PATENT NO. : 8,034,030 B2
APPLICATION NO. : 11/137284
DATED : October 11, 2011
INVENTOR(S) : Bernd Steinbach and Klaus G. Lederer Page 1 of 1

It is certified that error appears in the above-identified patent and that said Letters Patent is hereby corrected as shown below:

Cover page, under (57) Abstract, line 1 "pumps" should read --pump--.
Cover page, under (57) Abstract, line 9, "patient controlled" should read --patient-controlled--.
Column 1, line 32, "include" should read --includes--.
Column 1, line 53, "variable : flow rates," should read --variable flow rates,--.
Column 3, line 21, "assembly is preferably" should read --assembly preferably--.
Column 3, line 30, "patient" should read --patient.--.
Column 4, line 43, "second, replenishment" should read --second replenishment--.
Column 7, line 19, "located bottom" should read --located on bottom--.
Column 8, line 9, "which are smaller" should read --which is smaller--.
Column 10, line 18, "out (after" should read --out after--.
Column 10, lines 36-37, "near or in the" should read --near the--.
Column 11, line 35, "opening fluid" should read --opening in fluid--.
Column 11, line 36, "sealing first" should read --sealing the first--.
Column 12, line 15, "portion said" should read --portion of said--.

Signed and Sealed this
Eighteenth Day of December, 2012

David J. Kappos
*Director of the United States Patent and Trademark Office*